United States Patent
Fischer et al.

(10) Patent No.: US 11,160,295 B2
(45) Date of Patent: Nov. 2, 2021

(54) METHOD FOR PRODUCING A FOOD OR A PRECURSOR OF THE SAME, FOOD OR A PRECURSOR OF THE SAME AND A CORRESPONDING USE

(71) Applicant: Erdinger Weissbräu Werner Brombach GmbH & Co. KG, Erding (DE)

(72) Inventors: Malaika Fischer, Erding (DE); Peter Liebert, Erding (DE); Stefan Kreisz, Erding (DE)

(73) Assignee: Erdinger Weissbrau Werner Brombach GMBH & CO. KG

( * ) Notice: Subject to any disclaimer, the term of this patent is extended or adjusted under 35 U.S.C. 154(b) by 370 days.

(21) Appl. No.: 16/119,824

(22) Filed: Aug. 31, 2018

(65) Prior Publication Data
US 2019/0069579 A1    Mar. 7, 2019

(30) Foreign Application Priority Data

Sep. 4, 2017   (DE) .......................... 102017120283.8

(51) Int. Cl.

| | | |
|---|---|---|
| *C12C 11/06* | (2006.01) | |
| *C12C 11/00* | (2006.01) | |
| *A23L 2/38* | (2021.01) | |
| *A23L 2/52* | (2006.01) | |
| *A23L 33/135* | (2016.01) | |
| *C12N 1/20* | (2006.01) | |
| *A23L 31/15* | (2016.01) | |
| *C12C 12/00* | (2006.01) | |
| *C12C 5/02* | (2006.01) | |
| *A23L 33/15* | (2016.01) | |
| *A23L 33/14* | (2016.01) | |
| *C12N 1/18* | (2006.01) | |
| *C12C 3/00* | (2006.01) | |
| *A23L 33/145* | (2016.01) | |
| *A23L 29/00* | (2016.01) | |
| *C12R 1/225* | (2006.01) | |
| *C12R 1/865* | (2006.01) | |

(52) U.S. Cl.
CPC ................. *A23L 2/382* (2013.01); *A23L 2/52* (2013.01); *A23L 31/15* (2016.08); *A23L 33/14* (2016.08); *A23L 33/15* (2016.08); *C12C 5/023* (2013.01); *C12C 9/025* (2013.01); *C12C 11/003* (2013.01); *C12C 12/008* (2013.01); *C12N 1/185* (2021.05); *C12N 1/205* (2021.05); *A23L 29/065* (2016.08); *A23L 33/135* (2016.08); *A23L 33/145* (2016.08); *A23Y 2220/21* (2013.01); *C12R 2001/225* (2021.05); *C12R 2001/865* (2021.05)

(58) Field of Classification Search
CPC ........ C12C 11/06; C12C 11/00; C12C 12/008
See application file for complete search history.

(56) References Cited

U.S. PATENT DOCUMENTS

2006/0051323 A1    3/2006  Bijl et al.

FOREIGN PATENT DOCUMENTS

| DE | 102013100891 A1 | 7/2014 |
|---|---|---|
| DE | 102014110182 A1 | 1/2016 |
| EP | 0545139 B1 | 6/1993 |
| EP | 0824152 B1 | 11/2002 |
| EP | 2548948 A1 | 1/2013 |
| EP | 2995204 A1 | 3/2016 |
| EP | 3020285 A1 | 5/2016 |
| GB | 793467 | 4/1958 |
| JP | 58146292 A | 8/1983 |
| WO | WO 2008/010252 A2 | 1/2008 |
| WO | WO 2008/010252 A3 | 1/2008 |
| WO | WO 2009/124529 A2 | 10/2009 |
| WO | WO 2012/143469 A1 | 10/2012 |
| WO | WO 2013/084052 A1 | 6/2013 |
| WO | WO 2014/118191 A1 | 8/2014 |

OTHER PUBLICATIONS

Corsetti ("*Lactobacillus rossii* sp. nov., isolated from wheat Sourdough") International Journal of Systematic and Evolutionary Microbiology vol. 55, Issue 1, 35-40, 2005). (Year: 2005).*
DSMZ Catalogue ("*Loigolactobacillus coryniformis* subsp. Coryniformis DSM 20007". Leibniz Institute, Germany, available at https://www.dsmz.de/collection/catalogue/details/culture/DSM-20007, accessed on Jan. 4, 2021) (Year: 2021).*
Back ("Microbiology" Chapter 18, Handbook of Brewing: Process, Technology, Markets, Edited by Eblinger, 2009, 477-490, Wiley-VCH Berlag, Weinheim, Germanty, printed Darmstadt, Germany) (Year: 2009).*
Abbey ("On Brewing Bavarian Helles:Adapting to Inert Brewing" German Brewing Forum, www.germanbrewing.net, Aug. 2017) (Year: 2017).*
Maria De Angelis et al., "*Lactobacillus rossiae*, a Vitamin $B_{12}$ Producer, Represents a Metabolically Versatile Species within the Genus *Lactobacillus*", PLOS One, vol. 9, Issue 10, Sep. 2014, 11 pages.
Office Action dated Jul. 9, 2018 for DE Application No. 102017120283. 8, 5 pages.
Search Report dated Jan. 14, 2019 for EP Application No. 18190459. 0, 9 pages.

* cited by examiner

*Primary Examiner* — Robert J Yamasaki
*Assistant Examiner* — Charles Zoltan Constantine
(74) *Attorney, Agent, or Firm* — Patterson Thuente Pedersen, P.A.

(57) ABSTRACT

A method for producing a food or a precursor of the same, including the steps: (a) providing a mash or a wort or last runnings as a first nutrient medium; and (b) treatment of the first nutrient medium with lactic acid bacteria of the species *Lactobacillus rossiae* (DSM 15814$^T$) or with lactic acid bacteria of at least two kinds of species including *Lactobacillus rossiae* (DSM 15814$^T$). Furthermore, a corresponding food and corresponding uses are claimed.

41 Claims, No Drawings

METHOD FOR PRODUCING A FOOD OR A PRECURSOR OF THE SAME, FOOD OR A PRECURSOR OF THE SAME AND A CORRESPONDING USE

RELATED APPLICATION

The present application claims priority to German Application No. DE 10 2017 120 283.8 filed Sep. 4, 2017, which is hereby incorporated herein in its entirety by reference, including the English translation thereof.

TECHNICAL FIELD

Embodiments of present invention relates to a method for producing a food or a precursor of the same by treating a first nutrient medium with lactic acid bacteria of the species *Lactobacillus rossiae* (DSM 15814$^T$) or with lactic acid bacteria at least comprising two species including *Lactobacillus rossiae*, a food or a precursor of the same, as well as a use of the same.

BACKGROUND AND DEFINITIONS

Vitamin $B_{12}$ plays an essential role in cell division, hematopoiesis, performance of the neural system, in mental skills as well as in metabolization of carbohydrates, fats and proteins. Therefore, in case of a lack of Vitamin $B_{12}$, substantial metabolic defects or other physical impairments like for example a reduced energy metabolism or an affected immune system may appear.

A sufficient supply of the human or the animal body with Vitamin $B_{12}$ therefore represents an essential basis for health and performance capability.

Definitions

The term "food" or "foodstuff" means all substances and products according to embodiments of the invention, which are obvious to the person skilled in the art. Therefore, "food" may include all substances and products which are suitable for human or animal consumption and preferably exhibit a nutritional effect. In particular the term "food" may include within the scope of this application: a cereal-containing food, a cereal-containing bar, a malt extract product, breakfast cereals, pastries, a dairy product, a yoghurt, a beverage, a non-alcoholic beverage, a beer, a non-alcoholic beer, a wheat beer, a non-alcoholic wheat beer, a beer mixed beverage, a beverage fermented with yeast, a beverage fermented without yeast and/or concentrates of the aforementioned food. A precursor of the food according to embodiments of the invention, especially of the beverage may be Sauergut, a mash or a wort. Within the scope of this application the term "non-fluid" in context with food comprises a solid, pasty, pastelike, gelatinous, or likewise consistency or texture of a food.

Vitamin $B_{12}$ is a collective term for a series of water-soluble, structurally similar compounds with biologic effect, the so-called corrinoids. Based on the complexed cobalt atom they are denoted as cobalamines. The person skilled in the art numbers among the biologically active forms of Vitamin $B_{12}$ methylcobalamin, desoxyadenosylcobalamin, hydroxycobalamin and sulfitcobalamin. Among them, methylcobalamin and desoxyadenosylcobalamin are considered as the biologically most effective or most active forms. Of this group only cyanocobalamin is available via an artificial, that is, synthetic way.

Beside these active forms of Vitamin $B_{12}$ there are also so-called inactive analogues. These are also called pseudo-Vitamin $B_{12}$ because they exhibit indeed a similar chemical structure as the real Vitamin $B_{12}$, but they in some circumstances do not develop a vitamin-effect for the human or animal body. They are not appropriate in fulfilling physiologic functions of the Vitamins $B_{12}$ in the organism. Furthermore, they can block the incorporation and the metabolization of biologically active Vitamin $B_{12}$.

Within the scope of this application, pseudo-Vitamin $B_{12}$ especially means 7-adeninyl-cyanocobamide.

Within the scope of this application, the definition of the term "Vitamin $B_{12}$" is limited to the active forms of the Vitamin $B_{12}$ or their precursors which are active in the human or animal organism. Furthermore, the term "Vitamin $B_{12}$" within the scope of this application is limited to the forms of Vitamin $B_{12}$ which can be produced microbiologically. Whereas the aforementioned cyanocobalamin can only be produced via a synthetic way and therefore does not represent a "natural" Vitamin $B_{12}$, this form of Vitamin $B_{12}$ is not comprised in the term "Vitamin $B_{12}$" within the scope of this application.

Therefore, the definition of the term "Vitamin $B_{12}$" within the scope of this application is limited to the following Vitamin $B_{12}$ species: methylcobalamin, desoxyadenosylcobalamin, hydroxycobalamin and sulfitcobalamin.

The representatives of the aforementioned group are generally characterized by a high bioavailability so that these are appropriate in improving the supply of the human or the animal body with Vitamin $B_{12}$.

Within the scope of this application the term "bioavailability" means the resorption of the nutrient (Vitamin $B_{12}$) of the gastrointestinal tract into the blood by which it enters the systemic circulation and therefore, is available for the cells/organs. Furthermore, it is referred to the definition of the term "bioavailable" or "bioavailability" in paragraph [0013] of the description of the publication of the international patent application WO 2012/109 324 A1. The latter document is hereby incorporated by reference.

In order to determine bioavailable Vitamin $B_{12}$ detection analytics on basis of the so-called ADVIA-System was used. This proof of bioavailability is based on the so-called intrinsic factor (IF) and is for example used to detect bioavailable Vitamin $B_{12}$ in the blood. Vitamin $B_{12}$ is adsorbed in the last part of the small intestine (Ileum) via the intrinsic factor (IF=protein which is secreted in the parietal cells of the stomach lining). Within the scope of this test the IF-non-bound Vitamin $B_{12}$ is defined as non-bioavailable, since this does not enter the blood circulation and as a consequence thereof does not reach the corresponding tissue.

In the present application, the ADVIA Centaur VB12-Test (111659 Rev. N, 2008-09; VB12 2/12) was used to detect the bioavailable Vitamin $B_{12}$. This is a competitive immunoassay by using the direct chemiluminescence technology. By this, Vitamin $B_{12}$ in the assay competes with the acridiniumester marked Vitamin $B_{12}$ in a Lite reagent for a limited amount of cleaned IF which is covalently bound at paramagnetic particles in the solid phase. In this test, the releasing agent (sodium hydroxide) and DTT are used to release Vitamin $B_{12}$ from endogenous compound proteins in the assay. Added cobinamide prevents re-bonding after the addition of the solid phase to the assay.

In order to determine the (total) concentration of Vitamin $B_{12}$, which comprises all forms of Vitamin $B_{12}$, meaning bioavailable and non-bioavailable forms, the measurement method r-Biopharm AOAC-method No. 101002 is used within the scope of this application. Alternatively the method "Fresenius AOAC-Method No. 952.20" can be used to determine the total concentration.

In context with a yeast-product, the term "autolysate" according to embodiments of the invention means a nutrient substrate which is fluid in most cases and which is gained via dissolving the cells of yeast, fodder yeast (protein yeast) and/or especially beer yeast by intracellular enzymes.

In context with a yeast product, the term "extract" according to embodiments of the invention means a product of yeast-autolysate (produced by internal yeast enzymes) or yeast-hydrolysate (produced by external enzymes) which is powdery, gelatinous or pastelike in most cases and has a high content per dry mass of amino acids (for example 30 to 50%), carbohydrates (for example 20 to 30%) and vitamins (especially: B-group: thiamin, riboflavin, nicotinic acid). In general a yeast extract is produced by at least partially removing a yeast-autolysate or yeast-hydrolysate from insoluble cell components, concentrating and, if required, spray drying. Typically, a yeast extract exhibits a dry mass content of 70 to 80% in a pastelike consistency and 95 to 97% in a powder consistency.

The term "dried form" according to embodiments of the invention in context with a yeast product means any form of a yeast which comprises a water content of at most 5%, preferably of at most 2%, more preferably of at most 1%. Especially it means a dried yeast in form of flakes or powder or a freeze-dried yeast.

The term "Sauergut" within the scope of this application means the common definition within the field of brewing technology. Especially it means a microbial treated, preferably with lactic acid bacteria, nutrient medium for reducing the pH, especially a mash and/or wort.

Within the scope of this application the terms "mash", "wort" and "last runnings" mean especially the substrates which the person skilled in the art knows by the same expressions from the beer manufacturing process. The terms according to embodiments of the invention are not necessarily limited thereto but may refer to analogous substrates, meaning precursors in view of any beverage or any food like, for example, whiskey mashes. In particular, the wort according to embodiments of the invention may be produced by a mash according to the invention, as defined herein.

Preferably the term "mash" according to embodiments of the invention may be limited to a mash which was produced by using a carbohydrate-containing substrate or a mixture of carbohydrate-containing substrates. Thereby, the carbohydrate-containing substrate or the mixture of carbohydrate-containing substrates exhibits a proportion of brewer's malt of at least 80 mass %, more particularly at least 90 mass %, more particularly at least 95 mass %, more particularly at least 98 mass %, more particularly at least 99 mass %, and even more particularly about 100 mass %.

In particular, the term "mash" according to embodiments of the invention may be limited to a mash which was produced by using brewer's malt, wherein the brewer's malt comprises a proportion of wheat malt of at least 50 mass %, more particularly at least 52 mass %, and even more particularly at least 55 mass %. According to embodiments of the invention the term "brewer's malt" includes one single malt and also mixtures of different malts.

Furthermore, the term "wort" according to embodiments of the invention may be limited to a wort which was obtained by a mash which was produced by using brewer's malt with a proportion of wheat malt of at least 50 mass %, more particularly at least 52 mass %, and even more particularly at least 55 mass %. According to embodiments of the invention, the wort can be a wort which was produced of the mash as described before.

The term "hop bitter substances" within the scope of this application means all hop bitter substances and hop resins known to the person skilled in the art. These include both, soft resins and hard resins including bitter acids, especially the $\alpha$-acids and $\beta$-acids, and the known derivatives of these resins and acids, especially their oxidation products.

Within the scope of embodiments of the invention, the term "free of hop bitter substances" referring to a medium (e.g. nutrient medium or yeast product) means the complete absence of hop bitter substances in this medium.

The term "substantially free of hop bitter substances" referring to a first nutrient medium within the scope of this application means a content of hop bitter substances of at most 15%, more particularly at most 10%, more particularly at most 5%, and even more particularly at most 2%, referring to the content of hop bitter substances which a conventional brewery wort at pitching comprises for a fermentation with a bottom-fermenting or top-fermenting yeast with bitter units (EBC-method) in the range of 15 to 38, and even more particularly of 20 to 35. According to embodiments of the invention, the aforementioned percentages may also be applied to any single substance of the group of hop bitter substances (e.g. humulon or lupulon).

The term "substantially free of hop bitter substances" referring to a yeast product within the scope of this application means a content of hop bitter substances of at most 20%, more particularly at most 15%, more particularly at most 10%, more particularly at most 5%, and even more particularly at most 2%, referring to the content of hop bitter substances which is comprised a bottom-fermenting or top-fermenting process yeast of a brewery, in particular a freshly harvested yeast of the first, second or third generation which was harvested during a fermentation of a conventional brewery wort with bitter units (EBC-method) in the range of 15 to 38, and even more particularly 20 to 35. According to embodiments of the invention, the aforementioned proportions may also be applied to any single substance of the group of the hop bitter substances (e.g. humulon or lupulon).

Within the scope of this application, in analogous manner to the aforementioned definitions, also the term "hop bitter substances . . . completely or substantially completely removed . . . " referring to a yeast or a yeast product may be interpreted.

Within the scope of this application the term "beer" includes a partially or completely fermented beer, a beer ready for bottling, a filtered beer, a non-filtered beer, a light beer, a regular beer, a non-alcoholic beer, or a partly dealcoholized beer, a beverage based on wort or a beer mixed beverage as well as a precursor of the same. In particular, the term "beer" includes a wheat beer or a partially or fully dealcoholized or non-alcoholic wheat beer or mix beverages produced with the same.

The subject-matter of embodiments of the invention may refer to the production of alcoholic and non-alcoholic beverages in the brewery, in particular of beer, and the corresponding products. Within the scope of this application the terms "first wort", "boiling", "keeping hot", "trub", "pitching temperature", "pure culture yeast", "harvested yeast", "washing the yeast", "processing into a beverage", "wort acidification", "mash acidification" etc. are each referring to the meaning which a person skilled in the art in the field of beverage production, in particular in the field of beer production, usually refers to each of the terms or activities. The same is true in analog manner for using terms for subjects or activities within this application which refer to the production or treatment of solid or pastelike or gelatinous food and the corresponding products.

Within the scope of this application, the terms "treatment" or "treating" with lactic acid bacteria or yeast mean any kind of partial or complete metabolization of nutrients originating from a nutrient medium, in particular, a partial or complete fermentation by lactic acid bacteria. Moreover "treating" may be any kind of bringing microorganisms in contact or microorganisms being in contact, preferably lactic acid bacteria or yeast, in particular the lactic acid bacteria according to this application and beer yeast, with a nutrient medium.

The term "lactic acid bacteria" according to this application comprises any kind and state of lactic acid bacteria meaning any species or subspecies or any stem, as long this is not further limited in this application. Furthermore, this term comprises dead and/or living bacteria cells, in particular living bacteria cells. The DSMZ numbers used in this application are only for a distinct identification of the used bacteria species or bacteria subspecies according to embodiments of the invention. However, embodiments of the invention is not limited to the DSMZ as an exclusive source for the used bacteria species or bacteria subspecies according to the invention.

According to embodiments of the invention, "wheat beer" means a top-fermenting beer with a proportion of wheat malt of at least 50 mass %, more particularly at least 52 mass %, and even more particularly at least 55 mass %, in the malt grist or in the hydrocarbon-containing substrate.

The term "non-alcoholic" referring to a food, beverage or beer or any other product named in this application according to embodiments of the invention means a content of ethanol in the product of 0 to less than 1.2% by volume, more particularly of 0 to less than 1.0% by volume, more particularly of 0 to less than 0.5% by volume, more particularly of 0 to less than 0.3% by volume, more particularly of 0 to less than 0.1% by volume, and even more particularly about or exactly 0% by volume.

Within the scope of this application the specification "about", "approximately" or the like mean a relative deviation of the corresponding reference value of at most 10%, more particularly at most 5%, more particularly at most 3%, and even more particularly at most 1%.

The specifications regarding a volume or a volume fraction used in this application referring always to the temperature or the temperatures which a person skilled in the art would typically refer to the referring fluid or mixture for the corresponding purpose and the corresponding process step, as long as the temperature is not explicitly stated.

All masses and mass concentrations stated in the application refer to the corresponding dry mass of the corresponding substance.

State of the Art

In document EP 824 152 B1, the production of natural Vitamin $B_{12}$ in relatively high concentrations ((≥0.1 wt.-%) by using *Propionibacterium freudenreichii* is described.

Similarly, GB 793 467 A relates to the production of preparations which comprise a high Vitamin $B_{12}$ activity especially by cultivating a specific type of *Propionibacterium*, in particular *P. freudenreichii* or *P. shermanii*. Herein, a method for production of a physiologically active preparation of Vitamin $B_{12}$ is disclosed which is free of pseudo or inactive Vitamin $B_{12}$ variations.

However, it would be desirable if the amount or concentration of Vitamin $B_{12}$ which is contained in the products which are produced via the aforementioned procedures may be further increased.

SUMMARY AND DETAILED DESCRIPTION

An object of embodiments of the present invention is to provide an improved procedure for producing a food or a precursor of the same, in particular an Sauergut, a mash, a wort, a beverage or a non-fluid food, and the corresponding food or a precursor of the same, wherein this food or already a precursor of the same is able to further improve the supply of Vitamin $B_{12}$ of the human and/or animal body when ingesting this food or a precursor of the same.

One aspect of embodiments of the present invention is to provide a food or a precursor of the same which contains an elevated amount or concentration of Vitamin $B_{12}$.

A further aspect of embodiments of the present invention is to provide a food or a precursor of the same which was produced naturally and/or its raw materials are permitted by the German Purity Law or correspond to the German Purity Law, namely barley malt, wheat malt (or mixtures thereof), hops and water.

A further aspect of embodiments of this invention is to realize the object defined before and/or at least one of the aspects defined before in a simple technically and inexpensive way, especially by the equipment of a conventional brewery.

From a method's point of view, an object according to embodiments of the invention is solved by a method for producing a food or a precursor of the same. The procedure can comprise at least the following steps:

(a) providing a mash or a wort or last runnings as a first nutrient medium; and
(b) treating the first nutrient medium with lactic acid bacteria of the species *Lactobacillus rossiae* (DSM 15814$^T$ or DSM 15814) or with lactic acid bacteria comprising at least two species including *Lactobacillus rossiae* (DSM 15814$^T$).

By treating the first nutrient medium with the aforementioned lactic acid bacteria, a medium, in particular a Sauergut, is obtained which contains the Vitamin $B_{12}$. Thereby the inventors have surprisingly found out that just by using lactic acid bacteria of the species *Lactobacillus rossiae* (DSM 15814$^T$) elevated contents of the Vitamin $B_{12}$ may be obtained in the treated medium.

According to embodiments of the invention, the first nutrient medium is a mash or a wort, preferably a first wort or last runnings. Particularly, the first nutrient medium comprises an extract content in the range of 4 to 24° P, more particularly 5 to 20° P, more particularly 10 to 18° P, more particularly 12 to 17° P, and even more particularly 13 to 15° P.

In particular, when using mash or wort as a first nutrient medium, the applicant has surprisingly found out that the lactic acid bacteria used according to embodiments of the invention produce increasingly Vitamin $B_{12}$ in such a medium and are therefore suitable for the production of Vitamin $B_{12}$. Furthermore, it has been found out that the Vitamin $B_{12}$ produced by the used lactic acid bacteria according to embodiments of the invention is also bioavailable in the meaning of this application. In particular, in the first medium treated according to embodiments of the invention contents of bioavailable Vitamin $B_{12}$ may be obtained in the range of 5 to 15 µg/100 mL, and even more particularly 6 to 12 µg/100 mL (measured by ADVIA Centaur VB12-Test).

By using the method according to embodiments of the invention a further increased quantitative production of Vitamin $B_{12}$, in particular of bioavailable Vitamin $B_{12}$ may be obtained, obviously without a "switch" of the metabolism of the lactic acid bacteria according to embodiments of the invention to the production of the non-desired substances. Such a switch is known for example for lactic acid bacteria of other species like for example *Lactobacillus reuterii*.

Therefore, the method according to embodiments of the invention may comprise as step (b) the step:
(b) treating the first nutrient medium with lactic acid bacteria of the species *Lactobacillus rossiae* (DSM $15814^T$) and *Lactobacillus coryniformis*, in particular the subspecies *Lactobacillus coryniformis* subsp. *coryniformis* (DSMZ No. 20007), preferably with a mixture comprising lactic acid bacteria of the species *Lactobacillus rossiae* (DSM $15814^T$) and *Lactobacillus coryniformis*, in particular the subspecies *Lactobacillus coryniformis* subsp. *coryniformis* (DSMZ No. 20007).

Surprisingly, an even higher concentration of bioavailable Vitamin $B_{12}$ in the treated medium may be obtained by treating the first nutrient medium with a combination of *Lactobacillus rossiae* and *Lactobacillus coryniformis*.

The inventors have established a working hypothesis hereto and assume that the elevated yield of Vitamin $B_{12}$ is based on a synergy effect which is caused by the collaboration of *Lactobacillus rossiae* and *Lactobacillus coryniformis*. Therefore, it is assumed that the species *Lactobacillus rossiae* produces riboflavin which seems to be favorably used by the species *Lactobacillus coryniformis* for the synthesis of Vitamin $B_{12}$.

Therein, the volume ratio of the used lactic acid bacteria suspensions (*Lactobacillus rossiae* to *Lactobacillus coryniformis*) in step (b) may be between 10:90 to 85:15, more particularly 15:85 to 50:50, more particularly 15:85 to 35:65, and even more particularly 20:80 to 30:70, based/normalized on the same number of cells. By using the aforementioned volume ratios a high concentration of Vitamin $B_{12}$ is obtained in the treated medium according to the finding of the inventors.

In a further embodiment the treatment according to step (b) may be conducted in the presence of a yeast product, wherein the yeast product is an extract, an autolysate and/or contains a yeast in a fresh or dried form, or consists of an extract, an autolysate and/or a yeast in a fresh or dried form. According to embodiments of the invention the yeast product may also be or may also contain any mixture of an extract, an autolysate and/or a yeast in a fresh or dried form. In step (b) the mass concentration of the yeast product referring to the first medium may be ≥0.2 g/L, more particularly ≥4 g/L, more particularly ≥8 g/L, more particularly ≥15 g/L, and most particularly ≥18 g/L. Additionally or alternatively the mass concentration of the yeast product referring to the first nutrient medium in step (b) may be ≤70 g/L, more particularly ≤50 g/L, more particularly ≤40 g/L, more particularly ≤30 g/L, and most particularly ≤25 g/L. In particular, the mass concentration of the yeast product referring to the first nutrient medium in step (b) may be in the range of ≥0.2 to ≤70 g/L, more particularly of ≥8 to ≤50 g/L, more particularly of ≥12 to ≤40 g/L, and most particularly of ≥18 to ≤35 g/L.

Surprisingly, the amount and/or the mass concentration of Vitamin $B_{12}$ produced in the first nutrient medium may be increased by the presence of a yeast product or a combination of the described yeast products during the treatment of the first nutrient medium with lactic acid bacteria of the species *Lactobacillus rossiae* or a mixture of lactic acid bacteria containing this species, in particular a mixture of lactic acid bacteria of the species *Lactobacillus rossiae* (DSM $15814^T$) and *Lactobacillus coryniformis*.

Starting from the addition or mass concentration of the yeast product of about 0.2 g/L and in particular from 4 g/L (based on the first nutrient medium) an increase of the produced amount and/or mass concentration of Vitamin $B_{12}$ may be observed, even when the yeast product as such does not contain Vitamin $B_{12}$. Thereby, the additionally produced amount of Vitamin $B_{12}$ increases linearly at least over a certain range of concentration with the mass concentration of the yeast product which is present in the treatment.

However, beyond a mass concentration of the yeast product of about 70 g/L, in particular beyond 50 g/L (referring to the first nutrient medium) a strong sedimentation occurs in the reaction vessel and loss of quality of the produced food (or a precursor of the same) in view of the smell and the taste may be the consequence. This seems to be the result of an overload with cell material and its metabolic products.

High additions, such as, for example, additions beyond 20 g/L, and in particular beyond 50 g/L, may lead to unpleasant odor development if the yeast product is a fresh or dried yeast. It is assumed that this is a result of enhanced release of fatty acids and/or other metabolic products. In addition, the technical realization of the claimed procedure becomes less cost efficient by using high amounts of yeast products, preferably for mass concentrations beyond 20 g/L, and in particular beyond the concentration of 50 g/L.

Furthermore, if the step (b) should proceed in the presence of a yeast product, the yeast product may be heated or was heated before the implementation for example at 80° C. or more for 10 min or longer. The inventors have found out that the concentration of Vitamin $B_{12}$ in the medium may be obtained after the treatment according to step (b) according to the invention by sufficiently heating of the yeast product, compared to the case in which heating of the yeast product is omitted. It is assumed that by the influence of the heat the cell walls of the yeast cells are decomposed and/or a protein denaturation in the yeast product takes place which might have a positive effect on the yield of Vitamin $B_{12}$. It is especially favorable if the yeast product is heated together with the first nutrient medium, for example in form of a mixture before the implementation of the step (b), as described before. Thus, on the one hand a sterilization of the first nutrient medium and on the other hand the aforementioned effect of the increase of the Vitamin $B_{12}$ concentration after the treatment are achieved in one step.

In one particular embodiment, the production of the yeast product comprises a step in which a yeast is incubated at a temperature between 40 and 80° C., more particularly between 50 and 70° C., and even more particularly between 55 and 65° C. During the incubation, heating of the yeast to 80° C. or more, more particularly to 70° C. or more, and even more particularly to 65° C. or more, (depending on the incubation temperature), for 5 min or longer, and even more particularly for 10 min or longer should be ceased. If heating of the yeast to or above the aforementioned temperatures during incubation is ceased, thus, the inventors have found out that a higher concentration of Vitamin $B_{12}$ in the medium can be achieved after the treatment according to step (b) according to the procedure, compared to the case in which heating of the yeast takes place during incubation above the aforementioned temperatures. It is assumed that indeed by a limited heat flux (to about 60° C.), the cell walls of the yeast cells are decomposed and/or a protein denaturation in the yeast or yeast product takes place, which might have a positive effect on the yield of Vitamin $B_{12}$. However, when the thermal exposure is too high, a reduced concentration of Vitamin $B_{12}$ in the medium was measured after the treatment according to step (b). Furthermore the inventors have found out that heating of the yeast at the end of incubation or afterwards, for example for the purpose of pasteurization, is harmless concerning the yield of Vitamin $B_{12}$.

Furthermore, the first nutrient medium may be free or substantially free of hop bitter substances; and/or the yeast product may be free or substantially free of hop bitter substances.

The first nutrient medium and/or the yeast product may be taken from the brewing process. In particular the first nutrient medium may be a cast wort or wort at pitching. Furthermore, the yeast product may be a pure culture yeast, for example grown on hopped wort, or a harvested yeast, for example from the first, second or a higher generation. For these cases the inventors have found out that in the first nutrient medium and/or in the yeast product inhibitors may be included which may be harmful for the production of Vitamin $B_{12}$ by the proposed lactic acid bacteria. Probably these are the hop bitter substances.

According to the understanding of the inventors the hop bitter substances may be removed completely or substantially completely from the yeast product by for example washing the yeast product once or more with water, especially tap water or brewing water. The use of such a yeast product free of hop bitter substances in the process according to embodiments of the invention leads to an increase of the production of Vitamin $B_{12}$.

Similarly, an at least partially inhibition of the Vitamin $B_{12}$ production in the process according to embodiments of the invention could be determined if the first nutrient medium was not free or not substantially free of hop bitter substances. Thus, the use of a mash or a non-hopped wort, for example a first wort or non-hopped cast wort or wort at pitching, as a first nutrient medium, which is free of hop bitter substances, is favorable.

Furthermore, the yeast product may be produced form a top-fermenting or a bottom-fermenting yeast of the genus *Saccharomyces*, especially of the species *Saccharomyces cerevisiae* or the species *Saccharomyces carlsbergensis*. Thereby the yeast is a pure culture yeast or a harvested yeast of the beer manufacturing process. Furthermore, the hop bitter substances of the yeast or the yeast product are removed completely or substantially completely, for example by washing the yeast or the yeast product with water once or more times, especially tap water or brewing water.

By producing the yeast product of a conventional top-fermenting or bottom-fermenting brewery yeast, in particular of a harvested yeast, in case of the implementation of the process according to embodiments of the invention in a brewery an inexpensive and almost non-limited source in view of quantity for raw materials of the yeast product are available.

Beyond this, investigations have shown that a yeast product produced by using the aforementioned yeasts has a particular positive effect on the Vitamin $B_{12}$ production according to the process according to the invention.

In addition, the procedure may further comprise the steps:
(c) providing a mash or a wort as a second nutrient medium; and
(d) mixing the medium obtained in step (b) with the second nutrient medium.

By mixing the medium obtained in step (b) with a mash or a wort as a second nutrient medium, a biologic acidified mash or wort may be achieved by a simple further process step. The technological advantages of the biological mash or wort acidification are known to the person skilled in the art. Beyond the conventional advantages the process according to embodiments of the invention enables additionally the production of a mash or wort with an elevated content of bioavailable Vitamin $B_{12}$.

By using a mash or wort as a second nutrient medium it is advantageously achieved that the produced Vitamin $B_{12}$ is substantially quantitatively maintained and is not re-ingested or metabolized by the lactic acid bacteria. Beyond this, the Vitamin $B_{12}$ remains substantially completely or at least to a high proportion bioavailable. So a mash or wort may be produced which comprises a considerably higher content of Vitamin $B_{12}$ compared to conventional mashs or worts without being overacidified.

Thus, a mash produced according to the invention may comprise a pH-value in the range of 4.5 to 5.7, and more particularly 4.9 to 5.3. A wort produced according to embodiments of the invention may comprise a pH-value in the range of 4.2 to 5.7, and more particularly 4.6 to 5.0.

The adjustment of the pH-value of the mash or wort to the stated values leads to technological advantages like for example improved flavor stability, foam stability and brighter color of the beer.

The procedure may comprise further the steps:
(e) lautering the medium obtained in step (b) or (d);
(f) boiling of the medium obtained in step (d) or (e) or keeping the medium obtained in step (d) or (e) hot, and, hopping of the medium obtained in step (d) or (e);
(g) at least partly removing the trub from the medium obtained in step (f); and
(h) setting the temperature of the medium obtained in step (g) to a pitching temperature.

By applying the steps (e) to (h), the biologic acidified mash or wort according to embodiments of the invention may be further processed to a fermentable cast wort and wort at pitching which also comprises an elevated content of bioavailable Vitamin $B_{12}$.

Therefore, the procedure may obtain further at least one of the steps:
(i) processing the medium obtained in one of the steps (b), (d), (f), (g) or (h) result in a beverage, treating the medium with a yeast of the genus *Saccharomyces*, especially with the species *Saccharomyces cerevisiae* or the species *Saccharomyces carlsbergensis*; and/or
(k) mixing the medium obtained in one of the steps (b), (d), (f), (g) or (h) with a beverage, such as a beer.

The precursors obtained in the various process steps according to embodiments of the invention may be conventionally further processed, for example by alcoholic and non-alcoholic fermentation, into a beverage which also comprises an elevated content of bioavailable Vitamin $B_{12}$. This beverage may especially be: a non-alcoholic beverage, a beer, especially a non-alcoholic beer, a wheat beer, in particular a non-alcoholic wheat beer, a beer-containing beverage, especially a beer mixed beverage, a beverage being fermented with a yeast or being fermented not with a yeast. The beverage according to embodiments of the invention may also be simply obtained by mixing the precursors produced in the various process steps with a beverage, preferably with a beer. The beverage according to embodiments of the invention comprises an elevated content of bioavailable Vitamin $B_{12}$.

Despite the further increased content of Vitamin $B_{12}$ in the final beverage according to embodiments of the invention, an interference of the bioavailability or a depletion in the further process steps towards the final beverage does not or substantially does not take place according to the understanding of the inventors. Therefore, the same advantages of the treated first nutrient medium according to embodiments of the invention, especially the produced Sauergut, are also true for the produced beverage according to embodiments of the invention, especially for a beer and a non-alcoholic beer, in analog manner.

The process may further comprise the step:
(l) processing the medium obtained in one of the steps (b), (d), (f), (g) or (h) or the beverage obtained in step (i) or (k) to result in a non-fluid food;
wherein the medium obtained in one of the steps (b), (d), (f), (g) or (h) or the beverage obtained in step (i) or (k) is mixed with a precursor of the non-fluid food.

The precursors (treated media) or the beverage obtained in the various process steps according to embodiments of the invention may conventionally be further processed for example by concentrating and/or mixing with other components to a non-fluid food which also comprises an elevated content of bioavailable Vitamin $B_{12}$. This food may in particular be: a cereal-containing food, in particular a cereal-containing bar, breakfast cereals, a malt extract product, pastries, a diary product, in particular yoghurt.

Therefore, the advantages of the produced beverage according to embodiments of the invention are analogously valid for the aforementioned non-fluid food according to embodiments of the invention.

The mass proportion of water in the medium which was obtained in one of the steps (b), (d), (f), (g) or (h), in the beverage obtained by the step (i) or (k) or in the non-fluid food obtained by the step (l) may be adjusted to less than 35%, more particularly less than 30%, more particularly less than 25%, more particularly less than 20%, and even more particularly, less than 15%.

Higher water proportions than the aforementioned do not allow securing the microbiological stability of the food or a precursor of the same produced by the process according to embodiments of the invention. If the water content is adjusted by water removal, the costs for transport and storage of the concentrated medium are reduced by reduction of the volume.

Moreover, the concentrated medium may be customized by re-dilution to the original concentration or the desired concentration everywhere and independent of the place of production.

Furthermore, the concentrated medium comprises a higher viscosity compared to the starting material which is advantageously by using the concentrated medium for the production of food. Therefore, the concentrated medium may serve for example as a binder for granular or powdery food components.

Furthermore, it is advantageously if the mass fraction of water in the produced medium or beverage according to embodiments of the invention is adjusted to more than 0%, in particular to more than 5%.

By adjusting a defined residual water content the formation of dust during production or handling of the food or the precursor of the same is avoided.

Thereby, the advantages mentioned for the description of the method for production according to embodiments of the invention are analogously valid for a food or a precursor of the same produced by this method, especially a Sauergut, a mash, a wort, a beverage or a non-fluid food.

Furthermore, the use of lactic acid bacteria of the species *Lactobacillus rossiae* (DSM $15814^T$) or of lactic acid bacteria comprising at least two species including *Lactobacillus rossiae* (DSM $15814^T$), and more particularly a mixture of lactic acid bacteria of the species *Lactobacillus rossiae* (DSM $15814^T$) and *Lactobacillus coryniformis*, in particular the subspecies *Lactobacillus coryniformis* subsp. *coryniformis* (DSMZ No. 20007), is claimed for producing or in a method for producing a food or a precursor of the same, the method comprising at least the steps:

(a) providing a mash or a wort or last runnings as a first nutrient medium; and
(b) treating the first nutrient medium with lactic acid bacteria of the species *Lactobacillus rossiae* (DSM $15814^T$) or with lactic acid bacteria comprising at least two species, including *Lactobacillus rossiae* (DSM $15814^T$), and more particularly with a mixture containing lactic acid bacteria of the species *Lactobacillus rossiae* (DSM $15814^T$) and *Lactobacillus coryniformis*, in particular the subspecies *Lactobacillus coryniformis* subsp. *coryniformis* (DSMZ No. 20007).

In a particular embodiment, the treatment of step (b) takes place in presence of the yeast product wherein the yeast product preferably contains an extract, an autolysate and/or a yeast in fresh or dried form. Furthermore, the yeast product contains an extract, an autolysate and/or a yeast in fresh or dried form. The yeast product preferably may also consist of an extract, an autolysate and/or a yeast in fresh or dried form.

Particular embodiments of the use according to the invention are subject-matter of the dependent claims. Single or multiple features of the method according to embodiments of the invention mentioned before are able to be combined with the use according to embodiments of the invention. Thereby, the advantages of the corresponding features of the method according to embodiments of the invention are analogously valid.

Thus, the yeast product in a preferred embodiment of the use according to embodiments of the invention may be present in a mass concentration in the range of $\geq 0.2$ to $\leq 70$ g/L, more particularly from $\geq 8$ to $\leq 50$ g/L, based on the first nutrient medium.

Furthermore, the first nutrient medium may be free or substantially free of hop bitter substances. In addition or alternatively, the yeast product may be free or substantially free of hop bitter substances.

Alternatives and Further Disclosure of the Invention

Embodiments of the invention are not limited to the use or application of *Lactobacillus rossiae* (DSM $15814^T$ or 15814), and in particular, not to the combination of *Lactobacillus rossiae* (DSM $15814^T$) and *Lactobacillus coryniformis*. The manufacturing methods, uses and products as described above may alternatively be carried out or produced by a combination of *Lactobacillus rossiae* (DSM $15814^T$) together with lactic acid bacteria of the species *Lactobacillus backii* (DSM 18080), *Lactobacillus plantarum* (DSM 2648, DSM 2601, DSM 20174, DSM 13273) or *Lactobacillus fermentum* (DSM 20052), that is a mixture of lactic acid bacteria of *Lactobacillus rossiae* (DSM $15814^T$) and of at least one of the other species mentioned above or subspecies thereof. By doing so, the advantages, effects and properties as described above are achieved in analog manner.

In certain embodiments, a precursor of the yeast product, in particular a top fermenting or bottom fermenting pure culture yeast or harvested yeast of the brewery can be washed with water once or more times or any suitable substance. This may be performed by, for example, suspending the yeast cells with water and centrifuging them. After discarding the supernatant, the so washed yeast mass may be re-suspended in water and may be centrifuged subsequently. The steps of re-suspending and centrifuging may be repeated so many times until a desired degree of purity is achieved, especially until the yeast is free or substantially free of hop bitter substances.

In certain embodiments, a first wort of a brewery is selected as a first nutrient medium, wherein the first wort in step (a) exhibits an extract content in the range of 7 to 28%, more particularly 10 to 22%, more particularly 12 to 19%, and even more particularly 14 to 16%.

First wort as a first nutrient is characterized by a high content of nutrients essential for the lactic acid bacteria used in the procedure according to the invention. Moreover, the first wort is readily available and easily produced by the facilities of a conventional brewery.

In addition, a large width of concentration may be applied in view of the extract content of the first wort whereby the procedure is flexible in application.

The method according to embodiments of the invention is also applicable in high concentrated nutrient media which are obtained for example by high gravity brewing procedures by obtaining the associated benefits, especially savings in volume and costs.

In certain embodiments, before the treatment of the lactic acid bacteria (step (b)) the first nutrient medium is diluted with water, especially brewing water so that the extract content of the resulting diluent is in a range of 5 to 16%, more particularly 10 to 15%, and even more particularly 12 to 14%.

By a dilution of the first nutrient medium, the ideal nutrient concentration for the microorganisms used in the method according to embodiments of the invention may be adjusted.

Additionally the consumption of the first nutrient medium which is produced may be reduced.

The first nutrient medium may be inoculated with the lactic acid bacteria in an amount so that the optical density (OD) of the first nutrient medium is immediately after inoculation in the range of about 0.1 to 1.0 OD, more particularly 0.2 to 0.8, more particularly 0.3 to 0.7, more particularly 0.4 to 0.5 OD, and even more particularly about 0.45 OD, wherein the measurement value of the optical density is measured by a wave length of 620 nm and is corrected by the influence of the first nutrient medium.

Carrying out the inoculation of the first nutrient medium with the microorganisms used according to embodiments of the invention in a way that the aforementioned optical density (OD) or a corresponding cell density is adjusted at the beginning of the treatment, leads to a faster conversion and therefore, to a favorably shorter time of treatment.

Moreover, an ideal inoculation concentration of the lactic acid bacteria leads to an ideal flavor profile with minimal concentrations of off-flavors or to the complete absence thereof.

An optical density of the first nutrient medium immediately after the inoculation and if necessary, after homogenization of less than 0.4, more particularly 0.3, more particularly 0.2, and even more particularly 0.1 requires a too long time until a desirably high turnover rate of lactic acid bacteria is achieved.

In contrast, an optical density of the first nutrient medium of more than 0.5, more particularly 0.7, more particularly 0.8, and even more particularly 1.0, causes not ideal growth conditions for the lactic acid bacteria, for example due to feedback-inhibition, when the optical density is measured immediately after the inoculation and if necessary, after homogenization.

The lactic acid bacteria may be in the log phase (logarithmic phase) or growth phase at the beginning of the treatment of the first nutrient medium, in particular, when adding them to the first nutrient medium according to step (b).

An inoculation with microorganisms which are in the log phase or growth phase advantageously leads to a higher conversion of the first nutrient medium to a Sauergut, due to the high activity of the microorganisms applied.

The duration of the treatment according to step (b) may be about between 5 and 80 hours, more particularly 15 to 60, more particularly 20 to 50 hours, and even more particularly 20 to 30 hours.

The designated treatment period according to embodiments of the invention may be advantageously limited to the aforementioned short time periods. Hereby a prompt provision of a first nutrient medium, in particular, of a Sauergut may be realized. In particular, for a treatment time of less than 5 hours the yield of Vitamin $B_{12}$ and/or lactate is too low. In contrast, for a treatment time of more than 60 hours, in particular more than 80 hours, there is no further increase of the production of bioavailable Vitamin $B_{12}$. Furthermore there is a risk of overacidification.

The treatment according to step (b) may be performed at a temperature of the nutrient medium in the range of about 15 to 48° C., more particularly 25 to 42° C., more particularly 30 to 40° C., more particularly 35 to 39° C., and even more particularly 36 to 38° C.

The treatment according to step (b) may be performed advantageously in a broad temperature range. A selection of temperature between 30 and 40° C. creates ideal growth conditions for the used microorganisms wherein the required treatment period is shortened and an ideal quality of the resulting product is obtained.

Furthermore, the procedure may comprise a step in which the first nutrient medium treated according to step (b) is sterilized.

Due to a final sterilization step it can be excluded that the lactic acid bacteria used according to embodiments of the invention may have an undesirable effect on the respective product in further utilization of the product, for example in view of food or beverage production, especially in beer production.

Therefore, by using yeast in a later process step in particular their metabolization activities are not influenced negatively.

Sterilization can be performed by any means known to the person skilled in the art. The addition of the Sauergut to the boiling or hot wort is preferable.

The medium obtained in one of the steps (b), (d), (f), (g) or (h), the beverage obtained in step (i) or (k), or the non-fluid food obtained in step (l) may comprise a mass fraction of lactic acid in the range of about 0.1 to 1.0%, more particularly about 0.2 to 0.6%, more particularly about 0.3 to 0.5%, and even more particularly about 0.35 to 0.45%.

Due to the presence of lactic acid in the aforementioned mass fractions the produced medium according to embodiments of the invention, especially the Sauergut, may be used advantageously for setting of a particular pH-value of for example mash or wort. By this, an adjustment of the pH-value of food or corresponding precursors of the same, in particular of mash or wort, is achievable in a natural way and according to the German Purity Law.

The second nutrient medium may exhibit a temperature of at least 50° C., more particularly at least 60° C., more particularly at least 70° C., more particularly at least 80° C., more particularly at least 90° C., and even more particularly at least 95° C., during conducting step (d).

By the addition of the medium obtained in step (b) to the second nutrient medium at a high temperature an efficient inactivation or sterilization of at least a part of the lactic acid bacteria is obtained in one step. Hereby, an additional sterilization step is omitted as well as the efforts regarding costs, time and energy.

The medium obtained in step (b) may be added in a volume fraction of 2 to 20%, more particularly of 5 to 15%, more particularly 6 to 12%, more particularly 7 to 11%, and even more particularly 8 to 10%, referring to on the volume of the resulting mixture.

By adjusting such a volume fraction of the Sauergut to the resulting mixture, an ideal pH-value for the mash or wort may be obtained, which can comprise, for example, a pH-value of the resulting mixture in the range of 4.2 to 5.5, and even more particularly 4.6 to 5.3.

The treatment of the first nutrient medium with lactic acid bacteria according to step (b) may take place under substantially anaerobic conditions, in particular under anaerobic conditions.

The choice of anaerobic conditions or substantially anaerobic conditions during the treatment of the nutrient medium with the applied lactic acid bacteria according to embodiments of the invention possibly has a positive effect on quantity and/or bioavailability of the produced Vitamin $B_{12}$.

In embodiments, anaerobic conditions are produced by exclusion of air and/or by purging with $CO_2$ or $N_2$ or any other known measures. According to embodiments of the invention, "anaerobic conditions" mean an oxygen content of at most 0.1 mg/L, more particularly 0 mg/l, in the medium and/or in the gas phase above. According to embodiments of the invention "substantially anaerobic conditions" mean an oxygen content of at most 0.5 mg/L, more particularly at most 0.1 mg/l, in the medium and/or in the gas phase above and includes the condition which the person skilled in the art knows as "microaerophilic".

The produced food according to embodiments of the invention, in particular, the beverage, may be conformably with the German Purity Law or may be produced exclusively from ingredients which are approved for the production of beer according to the German Purity Law. Therefore, the raw materials of the food or beverage according to embodiments of the invention may be limited to the raw material approved according to the German Purity Law for brewing beer, in particular barley malt, wheat mal, hop, hop products, in particular hop extracts, and brewing water and the used microorganisms according to the invention including yeasts of the genus *Saccharomyces*. For the first time it is therefore possible to provide a food, especially a beverage with bioavailable Vitamin $B_{12}$ in elevated mass concentrations according to the German Purity Law.

In a particular embodiment of the procedure according to the invention, in a further step the lactate formed during treatment according to step (b) may be separated partially or completely by microfiltration, dialysis or any other suitable separation method. Hereby, the acidic taste impression is advantageously reduced or avoided at all, whereby the field of application of the resulting medium further broadens.

The food according to embodiments of the invention may exhibit a gelatinous or pastelike consistency. A gelatinous or pastelike consistency favors advantageously a faster or improved resorption of the nutrients therein, in particular of the Vitamins $B_{12}$ in the human or animal body. Furthermore, a gelatinous or pastelike consistency causes an improved compatibility and an easier edibility or handling, for example during consumption in sports or leisure activities.

The produced food according to embodiments of the invention may comprise a mass fraction of Vitamin $B_{12}$ of at least 0.15 μg per portion, more particularly at least 0.2 μg per portion, more particularly at least 0.3 μg per portion, more particularly at least 0.35 μg per portion, more particularly at least 0.4 μg per portion, more particularly at least 0.5 μg per portion, more particularly at least 0.6 μg per portion, more particularly at least 1.0 μg per portion, and even more particularly at least 1.5 μg per portion of the food, wherein the portion of the food exhibits a mass of 20 g.

The higher the mass fraction of Vitamin $B_{12}$ in the food according to embodiments of the invention, the better the achievable supply of Vitamin $B_{12}$ for the human or the animal body.

The produced food according to embodiments of the invention may comprise cereal components, such as, for example, malted and/or non-malted brewing cereals, in particular barley malt and/or wheat malt.

In particular during use of mash or wort as a first nutrient medium the applicant has surprisingly found out that the used lactic acid bacteria according to embodiments of the invention produce Vitamin $B_{12}$ in such a milieu and are therefore suitable for producing Vitamin $B_{12}$. Furthermore, it has been surprisingly found out that the Vitamin $B_{12}$ produced by the used lactic acid bacteria according to embodiments of the invention is also bioavailable in the sense of this application, completely or at least to a high portion. By applying the alternative procedure defined before, an active production of bioavailable Vitamin $B_{12}$ can also be achieved, obviously without the occurrence of a "switch" of the metabolism of the designated lactic acid bacteria according to the invention to the production of non-bioavailable Vitamin $B_{12}$.

The features named in context with embodiments of the invention described in this application depict, unless otherwise stated or apparent, optional features of particular embodiments which may be combined desirably with the subject-matters described herein and among themselves as long as the person skilled in the art does not observe any obvious hindrance to do so. Therefore, in particular all of the features of the procedures stated in this description can be also combined with the products described in this application and vice versa. In particular, all features named in context with the product according to embodiments of the invention are transferable to all further products described in this application and are therefore combinable. This is valid in analog manner for all procedures of this application and their features. This is valid in analog manner for the effects and advantages by the described features.

EXAMPLES

1. Removing the Yeast of Retardant, Especially of Hop Bitter Substances by Washing A top-fermenting or bottom-fermenting pure culture yeast or harvested yeast is suspended with brewing water in the ratio 1:9 (50 g process yeast+400 ml water). The resulting suspension is centrifuged for 5 min at 1000 G. Subsequently, the supernatant is discarded and the yeast sediment is re-suspended in 150 ml brewing water. The two last steps may be repeated two to three times.

After the washing, the yeast exhibits a pure, fresh, fruity smell. The originally existing bitterness is missing. In the microscopic compound the yeast cells seem to be intact. In the case of the bottom-fermenting yeast only few damaged cells are occurring. The washed yeast cells exhibit a homogeneous plasm besides the big, round cell nucleus. No cell wall cracks are observed. After vital stain the cells are still colorless (=alive).

2. Production of a Yeast Autolysate

The process of the yeast autolysis is can be initiated by cracking the cells. In order to do so, the yeasts are mechanically, thermically or chemically treated. The autolysis proceeds then during an incubation of the yeast for multiple hours or a plurality of days at 40 to 55° C. and at a suitable pH-value, such as, for example, at a pH-value in the range of 5 to 7.

A top-fermenting or bottom-fermenting pure culture yeast or harvested yeast is breeded in cast wort. The yeast exhibits a dry substance fraction of about 16 to 17%. It is harvested freshly and washed according to the procedure described before.

Optionally, the yeast cells may be pretreated for decomposition by one or more of the following procedures:
  a) wet cell decomposition with high-pressure homogenizer;
  b) ultrasonic treatment (with and without glass balls);
  c) vortexing (with and without glass balls); and
  d) addition of propionic acid.

Details according to the single pretreating processes are explained herein below.

The autolysis of the yeast cells itself then takes places by incubation of the possibly pretreated yeast cells for 24 hours at about 53° C. in the incubator (control amplitude: 50 to 55° C.) with permanent stirring of the batch. As a result a fluid autolysate is produced.

3. Production of a Yeast Extract (Variant of Autolysate)

The produced fluid autolysate as described before is concentrated by water removal. If required, it may be filtered and released from the substances impairing taste.

The main components of the so gained yeast extract are peptides and amino acids as a result of the protein breakdown as well as purines and pyrimidines which are formed by the enzymatic cleavage of the nucleic acids.

4. Details for the Pretreatment a) Wet Cell Decomposition with High-Pressure Homogenizer The mechanical decomposition of the yeast cells was performed with the high pressure homogenizer PANDA Plus 2000 from the company GEA Niro Soavi Germany. The wet cell decomposition by means of the high pressure homogenizer is the preferred decomposition procedure.

As a consequence of the specific fluid dynamics a stationary statistic vacuum (500 to 1500 bar, and more particularly 800 to 1200 bar) arises in the used homogenizer. Thereby, a formation of bubbles arises both within the yeast cell and at the boundary layer between the yeast cell wall and the surrounding medium (cavitation effect). When the vacuum is released at an expansion valve later, this leads to an implosion of the bubbles. This entails a selective rupture of the cell walls.

For preparing the yeast samples the freshly obtained process yeast is diluted with brewing water (1:2, v/v), carbonic acid is removed on the magnetic stirrer and subsequently washed three times according to the procedure described before.

Each yeast sample passes the decomposition procedure two times. The observation of the so treated cells by the light microscope reveals that the cells do not comprise any protoplast after the application of the homogenizer and only the cell shells remain in the compound.

The so decomposed yeast is incubated subsequently in the incubator for about 24 hours at about 53° C. and is autolyzed by the still intact enzymes. In order to stop the autolysis the batches are mashed for about 30 min.

Alternatively, the following procedures may be applied for cell decomposition:

b) Ultrassonicating (with and without Glass Balls)

The yeast sample is diluted with brewing water (10:90, v/v) and subsequently impinged with ultrasonic for 10 minutes (ultrasonic bath: MERCK eurolab USR 46 H).

For amplification of the mechanic forces small glass balls may be added to the yeast sample during the ultrasonic treatment (Company Prolabo/VWR, diameter of 2.5 to 3.5 mm).

c) Vortexing by a Test Tube Shaker (with and without Glass Balls)

The yeast sample is diluted with brewing water (10:90, v/v) and subsequently shaken or stirred intensively with a test tube shaker for one minute ("vortexing"; Vortex Genie 2-shaker: Bender & Hobein AG, level 8).

For amplification of the mechanic forces small glass balls may be added to the yeast sample during the ultrasonic treatment (Company Prolabo/VWR, diameter of 2.5 to 3.5 mm).

d) Addition of Propionic Acid

Propionic acid is added to the yeast sample so that the proportion of the acid in the mixture is 5 Vol.-%. The batch is shaken by hand and then by means of the vortexer. Subsequently the batch is shaken headlong for 15 minutes (TURBULA-Shaker). The samples are settled for 2 hours at room temperature and are shaken again.

5. Production of Dried Yeast and Yeast Flakes

The yeast suspension in a dry substance fraction of about 15% is sprayed uniformly on a hot roller (rolling dryer from the company VITAM GmbH, Hameln). The yeast cells crack during contacting the roller surface. Cell wall and cell content dry at the roller and are removed latest after 3 seconds as flakes. 10 L of yeast suspension give about 1.5 kg flakes. Subsequently, the yeast flakes are crushed in a mortar.

All of the yeast products named before and all further commercially available yeast products are checked in view of its content of Vitamin $B_{12}$: None of the yeast products comprised a detectable amount of Vitamin $B_{12}$.

Production of the Yeast Extract (Variant 1 of Dried Yeast)

20 g of a dried yeast of the stem W34/70 (Company Fermentis, Marcq en Baroeul/France) are suspended in 280 mL a flash pasteurized wort in a 500 mL bottle. Subsequently, the batch is left for 30 min and then is weakly stirred for 30 min (level 1 magnetic stirrer plate).

The batch as described before is incubated (heat stress) at about 57° C. for about 72 hours. Therein, the bottle is opened a little bit so that formed gas can escape.

The so obtained batch is centrifuged at 4500 G for 5 to 10 min. Subsequently, the supernatant is transferred in a sterile vessel. If the supernatant is still too turbid it is centrifuged again. The so obtained supernatant (ca. 250 mL) is the yeast extract according to this embodiment.

Production of the Yeast Extract (Variant 2 of Dry Yeast)

33.3 kg of a dried yeast of the stem W34/70 (Company Fermentis, Marcq en Baroeul/France) with a dried substance content of 20% are suspended in 150 L first wort in a container. Subsequently, the batch is left for 30 min.

The first wort used here is a non-hopped first wort with 16.5° Plato which was obtained of a mash with a bulk of at least 50% wheat malt. The first wort is pasteurized at 85° C. for about 10 min and is subsequently cooled to room temperature.

An amount of the first wort (ca. 350 L) produced and pasteurized as described before which was not used for the suspension of the dried yeast is heated in a Braun-fermenter at about 57° C. This heated first wort is added as the produced yeast suspension described before by which a total volume of about 500 L of the mixture results. The fermenter exhibits a rise volume of about 50%. The mixture is incubated or fermented at 57° C. for about 72 hours.

Subsequently, the content of the fermenter is pasteurized at 85° C. for about 10 min and subsequently cooled to about 5° C. Dead yeast cells and other solids are removed from the cooled batch by means of microfiltration or centrifugation by which the yeast extract ready to use results. Subsequently, the yeast extract can be stored till usage in a sterile container at 5° C.

Cultivation of the Lactobacills (Variant 1): *Lactobacillus rossiae* (DSM 15814)

500 mL MRS-medium (Company Merck, Darmstadt) were set and were autoclaved at 118° C. for 15 min. A lyophilisate of the lactobacills was suspended in the cooled MRS-medium and was incubated at 30° C. for 2 days. The so obtained batch was stored in the cooling room at 4° C.

For inoculation 7.5 mL of the aforementioned obtained batch are suspended in 500 mL fresh MRS-medium.

Cultivation of the Lactobacills (Variant 2): *Lactobacillus coryniformis* Subsp. *Coryniformis* (DSM 20001)

A non-hopped first wort with 16.5° Plato is provided which was gained of a mash with a bulk of at least 50% wheat malt. 17 L of the first wort are filled in a 20 L-Cornelius container respectively, are pasteurized/autoclaved at 101° C. for about 31 min and subsequently cooled to 37° C.

The so obtained medium is inoculated with 255 mL of the *Lactobacillus coryniformis* culture described above and fermented at 37° C. for 48 hours, by which a *Lactobacillus coryniformis* culture ready for use is resulting.

Cultivation of the Lactobacills: *Lactobacillus rossiae* (DSM 15814) (Variant 1)

500 mL of the MRS-medium (company Merck, Darmstadt) were set and were autoclaved for 15 min at 118° C. After cooling 5 g maltose and 5 g yeast extract (company Merck, Darmstadt) were added. Therein, the vessel is filled brimfully due to the fact that *Lactobacillus rossiae* is microaerophilic or anaerobic. A lyophilisate of the lactobacills was suspended in the MRS-medium and was incubated for 2 days at 30° C. The so obtained batch was stored in the cooling room at 4° C.

7.5 mL of the batch obtained before were suspended in 500 mL fresh MRS-medium for inoculation.

Cultivation of the Lactobacills: *Lactobacillus rossiae* (DSM 15814) (Variant 2)

A non-hopped first wort with 16.5° Plato is provided which was gained of a mash with a bulk of at least 50% wheat malt. 17 L of the first wort are filled in a 20 L-Cornelius container respectively, are pasteurized/autoclaved at 101° C. for about 31 min and subsequently cooled to 30° C.

The so obtained medium is inoculated with 255 mL of the *Lactobacillus rossiae* culture described above and fermented at 30° C. for 48 hours under anaerobic conditions, by which a *Lactobacillus coryniformis* culture ready for use is resulting. The anaerobic conditions were adjusted by overlaying the medium with $CO_2$ gas and fermentation in a closed container.

Production of Sauergut According to Embodiments of the Invention (Variant 1)

In a vessel of 100 mL the following ingredients are filled in brimfully:

72.4 mL flash pasteurized wort, 3 mL of the *Lactobacillus rossiae* culture as described above, 3 mL of the *Lactobacillus coryniformis* subsp. *coryniformis* culture as described above, and 33.6 mL yeast extract as described above.

This batch is homogenized and incubated at 30° C. for 2 days (step (b) of the method) by which a Sauergut is produced as a precursor of a food according to the invention.

Production of Sauergut According to Embodiments of the Invention (Variant 2)

775.7 L of a non-hoped first wort with 16.5° Plato which was obtained of a mash with a bulk of at least 50% wheat malt is provided. The first wort is mixed with 360 L of a yeast extract described before (produced according to the aforementioned Variant 2) in a fermenter, pasteurized at 80° C. for about 10 min and subsequently cooled to 37° C. The medium is overlayed for the production of anaerobic conditions with $CO_2$ gas. The so treated first nutrient medium is inoculated with a respective cultivation *Lactobacillus coryniformis* subsp. *coryniformis* (DSM 20001) and/or *Lactobacillus rossiae* (DSM 15814), or with a combination of *Lactobacillus rossiae* (DSM 15814) and *Lactobacillus paracasei* subsp. *paracasei* (DSM 4905), or of *Lactobacillus coryniformis* subsp. *coryniformis* (DSM 20001) and *Lactobacillus paracasei* subsp. *paracasei* (DSM 4905, each cultivated according to the Variant 2 described above) in a volume ratio of 1:1. The fermenter content is homogenized and is incubated at 37° C. for 2 days under slight stirring (step (b) of the method).

The fermentation may be stopped if the pH-value reaches a value of 3.7. For a defined stop of the fermentation the fermenter content may be pasteurized at 85° C. for 10 minutes. Furthermore, the lactate produced during the fermentation may be separated partially or completely by microfiltration, dialysis or another suitable separation method, if desired. Hereby, the acid taste of the formed Sauergut is reduced which may be desirable depending on the application. Furthermore, the dead cells are separated. Subsequently, there is the possibility to concentrate the so obtained Sauergut for example to 60° Brix in order to reduce the mass and costs of transportation of the so obtained food or a precursor of the same. The concentration step may be performed by means of a vacuum evaporator or another suitable process engineering.

Results

TABLE 1

Vitamin $B_{12}$ concentration after treatment of first nutrient medium

| Batch No. | First nutrient medium | Lactobacillus | Yeast product | Vitamin $B_{12}$ concentration [µg/100 mL] |
|---|---|---|---|---|
| A1 (blank) | wort | — | — | 0.05 |
| A2 | wort | L.c. | — | 0.58 |
| A3 | wort | L.r. | — | 0.33 |
| A4 | MRS | L.r. | Yeast extract (contained in MRS) | 1.53 |
| A5 | wort | L.r. | Yeast extract of fresh UG-yeast | 0.31 |

TABLE 1-continued

Vitamin $B_{12}$ concentration after treatment of first nutrient medium

| Batch No. | First nutrient medium | Lactobacillus | Yeast product | Vitamin $B_{12}$ concentration [µg/100 mL] |
|---|---|---|---|---|
| A6 | wort | L.r. + L.c. | Yeast extract of fresh UG-yeast | 4.52 |
| A7 | wort | L.r. + L.p. | Yeast extract of fresh UG-yeast | 0.35 |
| A8 | wort | L.c. + L.p. | Yeast extract of fresh UG-yeast | 0.32 |

L.r. = *Lactobacillus rossiae* (DSM 15814); L.c. = *Lactobacillus coryniformis* subsp. *coryniformis* (DSM 20001); L.p. = *Lactobacillus paracasei* subsp. *paracasei* (DSM 4905); A6, A7, A8: volume ratio of the lactobacills: 1:1 at normalized number of cells; UG = bottom fermenting; indicated is the total concentration of Vitamin $B_{12}$ in the batch, measured according to r-Biopharm AOAC-Methode Nr. 101002, wherein the bio-availability of the Vitamin $B_{12}$ formed was confirmed by means of the ADVIA Centaur VB12-Test.

As can be seen from Table 1 above, by the treatment of the first nutrient medium according to embodiments of the invention with *Lactobacillus rossiae* an elevated concentration of Vitamin $B_{12}$ compared to the check may be obtained (see batches No. A3 and A5 vs. A1). A further increase of the Vitamin $B_{12}$ concentration may be achieved by the presence of a yeast extract as it is comprised in the MRS-medium (see batch No. A4). A particular high concentration of Vitamin $B_{12}$ is obtained when a combination of *Lactobacillus rossiae* and *Lactobacillus coryniformis* is used for the treatment of the nutrient medium (see batch No. A6).

In contrast, by applying a combination of *Lactobacillus rossiae* and *Lactobacillus paracasei* a concentration of Vitamin $B_{12}$ which is achieved is about as high as in the case of the fermentation with only *Lactobacillus rossiae* (see batch A7 vs. A5). Also a combination of *Lactobacillus coryniformis* and *Lactobacillus paracasei* does not lead to an increase of Vitamin $B_{12}$ production compared to the use of only *Lactobacillus coryniformis* (see batch A8 vs. A2). Hereby, it is clearly demonstrated that very high concentrations of Vitamin $B_{12}$ is achieved by the combination of *Lactobacillus rossiae* and *Lactobacillus coryniformis*, however not by an arbitrary combination of species of lactobacills, even if these include either *Lactobacillus rossiae* or *Lactobacillus coryniformis*.

TABLE 2

Vitamin $B_{12}$ concentration and addition of yeast extract

| Batch No. | First nutrient medium | Lactobacillus | Yeast product | Vitamin $B_{12}$ concentration [µg/100 mL] |
|---|---|---|---|---|
| B1 (blank) | wort | — | — | 0.05 |
| B2 | wort | L.c. | — | 0.46 |
| B3 | wort | L.c. | Yeast extract of fresh UG-yeast | 1.29 |
| B4 | wort | L.c. | Yeast extract of dried UG-yeast | 1.78 |
| B5 | wort | L.c. + L.r. | Yeast extract of fresh UG-yeast | 4.24 |
| B6 | wort | L.c. + L.r. | Yeast extract of dried UG-yeast | 5.72 |

L.r. = *Lactobacillus rossiae* (DSM 15814); L.c. = *Lactobacillus coryniformis* subsp. *coryniformis* (DSM 20001); B5, B6: volume ratio of the lactobacills: 1:1 at a normalized number of cells; UG = bottom fermenting; indicated is the total concentration of Vitamin $B_{12}$ in the batch, measured according to r-Biopharm AOAC-Methode Nr. 101002, wherein the bio-availability of the Vitamin $B_{12}$ formed was confirmed by means of the ADVIA Centaur VB12-Test.

As can be seen from Table 2 above, by addition of a yeast extract of dried yeast compared to fresh yeast a further improved yield of Vitamin $B_{12}$ may be achieved.

TABLE 3

Vitamin $B_{12}$ concentration and presence of yeast extract

| Batch No. | First nutrient medium | Lactobacillus | Yeast product | Vitamin $B_{12}$ concentration [µg/100 mL] |
|---|---|---|---|---|
| C1 (blank) | wort | — | — | 0.05 |
| C2 | wort | L.r. | — | 0.13 |
| C3 | wort | L.c. + L.r. | — | 0.45 |
| C4 | wort | L.c. + L.r. | Yeast product of dried UG-yeast, 50% | 4.93 |
| C5 | wort | L.c. + L.r. | Yeast extract of dried UG-yeast, 40% | 4.93 |
| C6 | wort | L.c. + L.r. | Yeast extract of dried UG-yeast, 30% | 5.33 |

L.r. = *Lactobacillus rossiae* (DSM 15814); L.c. = *Lactobacillus coryniformis* subsp. *coryniformis* (DSM 20001); C3 to C6: volume ratio of the lactobacills: 1:1 at a normalized number of cells; UG = bottom fermenting; indicated is the total concentration of Vitamin $B_{12}$ in the batch, measured according to r-Biopharm AOAC-Methode Nr. 101002, wherein the bio-availability of the Vitamin $B_{12}$ formed was confirmed by means of the ADVIA Centaur VB12-Test.

As can be seen from Table 3 above, this batch also confirms that by the treatment of the wort as the first nutrient medium according to embodiments of the invention with *Lactobacillus rossiae* an elevated concentration of Vitamin $B_{12}$ compared to the blank batch may be obtained. A further significant increase of the Vitamin $B_{12}$ concentration may be achieved by the combined treatment of *Lactobacillus rossiae* and *Lactobacillus coryniformis*. The yield of Vitamin $B_{12}$ further increases significantly in the presence of a yeast extract. Here, a proportion of yeast extract of 50% is not necessary, with a volume fraction of 30% the highest vitamin concentration was achieved in this test series.

Taste testings revealed that the beers produced by means of Sauergut which was produced by the method according to embodiments of the invention exhibited a smell which reminds of bread or sourdough. In particular, this was the case when using yeast extract of fresh yeast. In case of using an addition of dried yeast, the intensity of sourdough bread was significantly less. An analogous impression was observed in view of the taste evaluation of the beers.

In a further batch it should be found out which amount of yeast extract would cause the highest yield of bioavailable Vitamin $B_{12}$. For this purpose, the added amounts of yeast extract were varied at same conditions.

TABLE 4

Vitamin $B_{12}$ concentration and amount of yeast product

| Batch No. | Yeast product (vol.-%, referring to the first nutrient medium) | Yeast product (g/L, referring to the volume of the first nutrient medium) | Vitamin $B_{12}$ concentration [µg/100 mL] |
|---|---|---|---|
| D1 (blank) | 0 | 0 | 0.62 |
| D2 | 5 | 3.8 | 1.92 |
| D3 | 10 | 7.9 | 2.92 |
| D4 | 20 | 17.9 | 4.48 |
| D5 | 30 | 30.6 | 4.88 |
| D6 | 40 | 47.6 | 3.14 |
| D7 | 50 | 71.4 | 2.46 |

Used first nutrient medium: wort; used lactobcilli: mixture of *Lactobacillus rossiae* (DSM 15814) and *Lactobacillus coryniformis* subsp. *coryniformis* (DSM 20001); each with the volume ratio 1:1 at a normalized number of cells; yeast product: yeast extract of a bottom fermenting dried yeast, produced by the aforementioned Variant 1; indicated is the total concentration of Vitamin $B_{12}$ in the batch, measured according to r-Biopharm AOAC-Methode Nr. 101002, wherein the bio-availability of the Vitamin $B_{12}$ formed was confirmed by means of the ADVIA Centaur VB12-Test.

As can be seen from Table 4 above, due to the addition of a yeast product already at an amount of 3.8 g yeast extract to 1 L of the first nutrient medium (corresponds to 5 vol.-% used yeast extract based on the first nutrient medium) an elevated concentration of bioavailable Vitamin $B_{12}$ was detected. By an addition of about 30 g yeast extract to 1 L first nutrient medium (corresponding to 30 vol.-% used yeast extract based on the first nutrient medium), the highest concentration with almost 5 µg/100 mL was detected. If the addition of the yeast extract is further increased to about 70 g/L, high concentrations of bioavailable Vitamin $B_{12}$ in the nutrient medium are achieved. However, the produced amounts decrease again. According to this batch, an addition amount of yeast product between 4 and 70 g/L, more particularly between 8 and 50 g/L, more particularly between 12 and 40 g/L, and even more particularly between 18 and 35 g/L, referring to the volume of the first nutrient medium seems to result in a particular high yield.

In a further batch it should be found out how the incubation temperature of the yeast affects the production of bioavailable Vitamin $B_{12}$ during the production of the yeast product in the production method according to the invention. In order to do so, a yeast extract was produced as a yeast product from bottom fermenting dried yeast according to the Variant 1 described before, wherein the incubation was performed once at 57° C. (standard procedure) and was performed by the variant of 80° C. Additionally, the concentration of the yeast product was varied. All other conditions were the same.

TABLE 5

Vitamin $B_{12}$ concentration and Incubation temperature

| Batch No. | Yeast product [g/L; referring the volume of the first nutrient medium] | Incubation temperature [° C.] | Vitamin $B_{12}$ concentration [µg/100 mL] |
|---|---|---|---|
| E1 (blank) | 0 | 57 | 0.52 |
| E2 | 17.9 | 57 | 3.84 |
| E3 | 35.7 | 57 | 5.60 |
| E4 | 35.7 | 80 | 0.20 |
| E5 | 71.4 | 57 | 8.96 |
| E6 | 71.4 | 80 | 0.32 |

Used first nutrient medium: wort; used lactobacilli: mixture of *Lactobacillus rossiae* (DSM 15814) and *Lactobacillus coryniformis* subsp. *coryniformis* (DSM 20001); each with the volume ratio 1:3 at normalized number of cells; yeast product: yeast extract of bottom fermenting dried yeast, produced by the aforementioned Variant 1 with the incubation temperature 57 or 80° C.; indicated is the total concentration of Vitamin $B_{12}$ in the batch, measured according to r-Biopharm AOAC-Methode Nr. 101002, wherein the bio-availability of the Vitamin $B_{12}$ formed was confirmed by means of the ADVIA Centaur VB12-Test.

As can be seen from Table 5 above, during this study an increasing concentration of bioavailable Vitamin $B_{12}$ was observed with an increasing amount of yeast product (incubation at 57° C.). However, when the incubation temperature was increased from 57° C. to 80° C. during the production of the yeast extract at otherwise same conditions, a significantly lower concentration of Vitamin $B_{12}$ resulted.

Variation of the Mixing Ratio of the Lactobacilli

In a further study it was investigated if the yield of Vitamin $B_{12}$ may be further increased, if both of the used lactic acid bacteria *Lactobacillus rossiae* and *Lactobacillus coryniformis* subsp. *coryniformis* are used in different mixing ratios.

For all batches 72 mL wort with 33 mL dried yeast and 6 mL suspension of bacteria (in MRS) were mixed wherein each of the suspension of bacteria comprises the following composition:

Batch F2: 1.5 mL *L. coryniformis*+4.5 mL *L. rossiae*
Batch F3: 3.0 mL *L. coryniformis*+3.0 mL *L. rossiae*
Batch F4: 4.5 mL *L. coryniformis*+1.5 mL *L. rossiae*

The respective batch was incubated in the incubator for 48 h at 37° C. Subsequently, the batches were heated in the water bath for 30 min at 95° C. The samples were deep-frozen till the determination of Vitamin $B_{12}$.

The contents of Vitamin $B_{12}$ were determined microbiologically: 20 mL sample+20 mL (Na-acetate pH 4.5+1% KCN+α-amylase, pepsin).

The further implementation was performed according to the method r-Biopharm AOAC-method No. 101002.

TABLE 6

Vitamin $B_{12}$ concentration and mixing ratio of Lactobacilli

| Batch No. | First nutrient medium | Lactobacilli (volume ratio L.c.:L.r.) | Vitamin $B_{12}$ concentration [µg/100 mL] |
|---|---|---|---|
| F1 (blank) | Wort | — | 0.05 |
| F2 | Wort | 1:3 | 1.60 |
| F3 | Wort | 1:1 | 2.54 |
| F4 | Wort | 3:1 | 2.86 |

Indicated is the total concentration of Vitamin $B_{12}$ in the batch, measured according to r-Biopharm AOAC-Methode Nr. 101002, wherein the bio-availability of the Vitamin $B_{12}$ formed was confirmed by means of the ADVIA Centaur VB12-Test.

As can be seen from Table 6 above, the increase of the Vitamin $B_{12}$-synthesis may be achieved for an increasing *L. coryniformis* proportion in the inoculum. The absolute concentrations are only to a limited extent comparable to the aforementioned experimental results based on the different states of the lactobacills used.

As a consequence, the proportion of *L. coryniformis* in the used mixture of lactobacills is at least 50 vol.-%, and more particularly 60 to 90 vol.-%.

Comparison to Prior Art

Conventionally, for the acidification of the mash or the wort the species *Lactobacillus amylovorus* or *Lactobacillus amylolyticus* are used which proved for many years in the production of the corresponding Sauergut and the mashes and worts acidified with those.

Therefore, these lactic acid species are characterized by a growth dominance in beer wort due to fast growth. Furthermore, they are characterized by high souring due to a high lactate production. This is based on their homo-fermentative metabolism character. These species grow at high temperatures (to 52° C.) so that high reproduction rates may be obtained.

Furthermore, these species are able to ferment dextrin and starch. Further, they produce a high proportion of L(+)-lactate. The named lactic acid bacteria are not harmful to beer due to the fact that they are hop sensitive and cannot grow at temperatures <30° C. which is of significant importance. Among experts, *Lactobacillus amylovorus* and *Lactobacillus amylolyticus* are therefore regarded as suitable organisms for acidification due to the fact that they do not form amines (histamine) or other toxins. Furthermore, they do not form diacetyl or other disadvantageous substances for taste and favor of the resulting products. Finally, they are characterized by easy handling in practical application.

On the other hand, the species *Lactobacillus rossiae* according to embodiments of the invention, which can be used in combination with *Lactobacillus coryniformis* according to embodiments of the invention, is considered by experts as a beer spoilage organism. This is also valid for the species *Lactobacillus coryniformis*. *Lactobacillus rossiae* is known to the person skilled in the brewing art as a slime former. Both species grow in weakly hopped beer and form diacetyl which leads to a disadvantageously taste profile in the resulting food or beverage, in particular, in the beer. Further, they are able to grow at the conventional beer fermenting temperatures, especially for top-fermenting beer, namely in the range of 15 to 48° C. Furthermore, these species exhibit the disadvantage compared to the species *Lactobacillus amylovorus* and *Lactobacillus amylolyticus* conventionally used for acidification that this species is optionally hetero-fermentative, meaning their ability to acidify, is reduced compared to the conventionally used species. As a result about the double amount of Sauergut has to be used compared to conventionally used species. Hereby, larger production facilities are required and the costs linked to the acidification increase.

The aforementioned plurality of disadvantages as well as the disadvantages known by the person skilled in the art of the species *Lactobacillus rossiae* and *Lactobacillus coryniformis* examined here means a substantial hindrance for the application of these species or subspecies of the same in the beverage and food producing industry, especially in breweries and malteries, until now.

The invention claimed is:

1. A method for producing a food or a precursor of the same, the method comprising:
   (a) providing a mash or a wort or last runnings as a first nutrient medium; and
   (b) treating the first nutrient medium with lactic acid bacteria of the species *Lactobacillus rossiae* (DSM 15814$^T$) or with lactic acid bacteria at least comprising two species including *Lactobacillus rossiae* (DSM 15814$^T$).

2. The method according to claim 1, wherein step (b) includes:
   treating the first nutrient medium with a mixture comprising lactic acid bacteria of the species *Lactobacillus rossiae* (DSM 15814$^T$) and *Lactobacillus coryniformis*.

3. The method according to claim 2, wherein the species *Lactobacillus coryniformis* is subspecies *Lactobacillus coryniformis* subsp. *coryniformis* (DSMZ No. 20007).

4. The method according to claim 1, wherein the treatment according to step (b) takes place in the presence of a yeast product in the first nutrient medium.

5. The method according to claim 4, wherein the yeast product is selected from the group consisting of an extract, an autolysate, a yeast in fresh form, a yeast in dried form, and combinations thereof.

6. The method according to claim 4, wherein the yeast product is present at a mass concentration in the range of from ≥0.2 to ≤70 g/L, referring to the first nutrient medium.

7. The method according to claim 6, wherein the mass concentration of yeast product is in the range of from ≥8 to ≤50 g/L, referring to the first nutrient medium.

8. The method according to claim 4, wherein at least one of the first nutrient medium and the yeast product is free or substantially free of hop bitter substances,
   wherein the hop bitter substances include soft resins and hard resins including bitter acids and the known derivatives of these resins and acids; and
   wherein the first nutrient medium is substantially free of hop bitter substances when a content of hop bitter substances is of at most 15% referring to a content of hop bitter substances which a conventional brewery wort at pitching comprises for a fermentation with a bottom-fermenting or top-fermenting yeast with bitter units in a range of 15 to 38, measured according to an EBC-method; and
   wherein the yeast product is substantially free of hop bitter substances when a content of hop bitter substances is of at most 20% referring to a content of hop bitter substances which is comprised in a freshly harvested yeast of a first, second, or third generation which was harvested during a fermentation of a conventional brewery wort with bitter units in a range of 15 to 38, measured according to an EBC-method.

9. The method according to claim 4, wherein the yeast product is obtained from a top-fermenting or bottom-fermenting brewery yeast of the genus *Saccharomyces*.

10. The method according to claim 9, wherein the yeast product is obtained from a top-fermenting or bottom-fermenting brewery yeast of the species *Saccharomyces cerevisiae* or of the species *Saccharomyces carlsbergensis*.

11. The method according to claim 9, wherein the yeast is a pure culture yeast or a harvested yeast from the beer production process.

12. The method according to claim 9, wherein hop bitter substances are removed completely or substantially completely from the yeast or the yeast product;
   wherein the hop bitter substances include soft resins and hard resins including bitter acids and the known derivatives of these resins and acids; and
   wherein hop bitter substances are substantially completely removed from the yeast or yeast product when a content of hop bitter substances is at most 20% referring to the content of hop bitter substances which is comprised in a freshly harvested yeast of a first, second, or third generation which was harvested during a fermentation of a conventional brewery wort with bitter units in a range of 15 to 38, measured according to an EBC-method.

13. The method according to claim 1, the method further comprising:
   (c) providing a mash or a wort as a second nutrient medium; and
   (d) mixing the treated first nutrient medium obtained in step (b) with the second nutrient medium.

14. The method according to claim 13, the method further comprising:
   (i) processing medium obtained in step (d) to result in a beverage, and/or
   (k) mixing the medium obtained in step (d) with a beverage.

15. The method according to claim 14, wherein step (i), if present, comprises treating the medium with a yeast of the genus *Saccharomyces*, and wherein the beverage in step (k), if present, comprises beer.

16. The method according to claim 14, the method further comprising:
   (t) adjusting a mass fraction of water in the beverage obtained in step (i) or (k), wherein the mass fraction is adjusted to one of: less than 35%, less than 30%, less than 25%, less than 20%, and less than 15%; and to more than 0% or more than 5%.

17. The method according to claim 14, wherein the method further comprises the step:
   (l) processing the beverage obtained in the step (i) or (k) to result in a non-fluid food, wherein the beverage obtained in step (i) or (k) is mixed with a precursor of the non-fluid food.

18. The method according to claim 17, the method further comprising:
  (t) adjusting a mass fraction of water in non-fluid food obtained in step (1), wherein the mass fraction is adjusted to one of: less than 35%, less than 30%, less than 25%, less than 20%, and less than 15%; and to more than 0% or more than 5%.

19. The method according to claim 13, the method further comprising:
  (e) optionally lautering medium obtained in step (d);
  (f) boiling medium obtained in step (d) or (e) or keeping the medium obtained in step (d) or (e) hot, and optionally hopping of the medium obtained in step (d) or (e);
  (g) optionally, at least partly removing trub from the medium obtained in step (f); and
  (h) optionally, setting the temperature of the medium obtained in step (f) or (g) to a pitching temperature.

20. The method according to claim 19, the method further comprising:
  (i) processing medium obtained in claim 19 to result in a beverage, and/or
  (k) mixing the medium obtained in claim 19 with a beverage.

21. The method according to claim 20, wherein step (i), if present, comprises treating the medium with a yeast of the genus *Saccharomyces*, and wherein the beverage in step (k), if present, comprises beer.

22. The method according to claim 20, the method further comprising:
  (t) adjusting a mass fraction of water in the beverage obtained in step (i) or (k), wherein the mass fraction is adjusted to one of: less than 35%, less than 30%, less than 25%, less than 20%, and less than 15%; and to more than 0% or more than 5%.

23. The method according to claim 20, wherein the method further comprises the step:
  (l) processing the beverage obtained in the step (i) or (k) to result in a non-fluid food, wherein the beverage obtained in step (i) or (k) is mixed with a precursor of the non-fluid food.

24. The method according to claim 23, the method further comprising:
  (t) adjusting a mass fraction of water in non-fluid food obtained in step (1), wherein the mass fraction is adjusted to one of: less than 35%, less than 30%, less than 25%, less than 20%, and less than 15%; and to more than 0% or more than 5%.

25. The method according to claim 1, the method further comprising:
  (e) optionally lautering medium obtained in step (b);
  (f) boiling of the medium obtained in step (b) or (e) or keeping the medium obtained in step (b) or (e) hot, and optionally hopping of the medium obtained in step (b) or (e), lautered or unlautered;
  (g) optionally, at least partly removing trub from the medium obtained in step (f); and
  (h) optionally, setting the temperature of the medium obtained in step (f) or (g) to a pitching temperature.

26. The method according to claim 25, the method further comprising:
  (i) processing medium obtained in claim 25 to result in a beverage, and/or
  (k) mixing the medium obtained in claim 25 with a beverage.

27. The method according to claim 26, wherein step (i), if present, comprises treating the medium with a yeast of the genus *Saccharomyces*, and wherein step (k), if present, comprises mixing the medium with beer.

28. The method according to claim 26, the method further comprising:
  (t) adjusting a mass fraction of water in the beverage obtained in step (i) or (k), wherein the mass fraction is adjusted to one of: less than 35%, less than 30%, less than 25%, less than 20%, and less than 15%; and to more than 0% or more than 5%.

29. The method according to claim 26, wherein the procedure further comprises:
  (l) processing the beverage obtained in the step (i) or (k) to result in a non-fluid food, wherein the beverage obtained in step (i) or (k) is mixed with a precursor of the non-fluid food.

30. The method according to claim 29, the method further comprising:
  (t) adjusting a mass fraction of water in the non-fluid food obtained in step (1) to one of: less than 35%, less than 30%, less than 25%, less than 20%, and less than 15%; and to more than 0% or more than 5%.

31. The method according to claim 1, the method further comprising:
  (i) processing medium obtained in step (b) to result in a beverage, and/or
  (k) mixing the medium obtained in step (b) with a beverage.

32. The method according to claim 31, wherein step (i), if present, comprises treating the medium with a yeast of the genus *Saccharomyces*, and wherein step (k), if present, comprises mixing the medium with beer.

33. The method according to claim 31, the method further comprising:
  (t) adjusting a mass fraction of water in the beverage obtained in step (i) or (k), wherein the mass fraction is adjusted to one of: less than 35%, less than 30%, less than 25%, less than 20%, and less than 15%; and to more than 0% or more than 5%.

34. The method according to claim 31, wherein the procedure further comprises:
  (l) processing the beverage obtained in the step (i) or (k) to result in a non-fluid food, wherein the beverage obtained in step (i) or (k) is mixed with a precursor of the non-fluid food.

35. The method according to claim 34, the method further comprising:
  (t) adjusting a mass fraction of water in the non-fluid food obtained in step (1) to one of: less than 35%, less than 30%, less than 25%, less than 20%, and less than 15%; and to more than 0% or more than 5%.

36. A method of using lactic acid bacteria for producing a beverage or a precursor of the same, the method comprising:
  utilizing lactic acid bacteria of the species *Lactobacillus rossiae* (DSM 15814,) lactic acid bacteria of at least comprising two species including *Lactobacillus rossiae* (DSM 15814T), or a mixture containing lactic acid bacteria of the species *Lactobacillus rossiae* (DSM 158141) and *Lactobacillus coryniformis* to treat a first nutrient medium, wherein the first nutrient medium comprises a mash, a wort, or last running.

37. The method of claim 36,
  wherein the first nutrient medium optionally further comprises a yeast product, and
  wherein the yeast product, if present, comprises an extract, an autolysate, a fresh form of a yeast, or a dried form of yeast, or combinations thereof.

38. The method of claim 37, wherein the yeast product, if present, is present in a mass concentration in the range from ≥0.2 to ≤70 g/L, referring to the first nutrient medium.

39. The method of claim 38, wherein the mass concentration of yeast product, if present, is in the range from ≥8 to ≤50 g/L, referring to the first nutrient medium.

40. The method of claim 37, wherein first nutrient medium is free or substantially free from hop bitter substances, the yeast product, if present, is free or substantially free of hop bitter substances, or a combination thereof;
- wherein the hop bitter substances include soft resins and hard resins including bitter acids and the known derivatives of these resins and acids; and
- wherein "substantially free of hop bitter substances" referring to the first nutrient medium means a content of hop bitter substances of at most 15% referring to the content of hop bitter substances which a conventional brewery wort at pitching comprises for a fermentation with a bottom-fermenting or top-fermenting yeast with bitter units in the range of 15 to 38, measured according to the EBC-method; and
- wherein "substantially free of hop bitter substances" referring to the yeast product means a content of hop bitter substances of at most 20% referring to the content of hop bitter substances which is comprised in a freshly harvested yeast of the first, second or third generation which was harvested during a fermentation of a conventional brewery wort with bitter units in the range of 15 to 38, measured according to the EBC-method.

41. The method of claim 36, wherein utilizing comprises: utilizing a mixture of lactic acid bacteria of the species *Lactobacillus rossiae* (DSM 15814$^T$) and *Lactobacillus coryniformis*, and wherein the species *Lactobacillus coryniformis* is subspecies *Lactobacillus coryniformis* subsp. *coryniformis* (DSMZ No. 20007).

* * * * *